US00PP15358P2

(12) United States Plant Patent
Oliver

(10) Patent No.: US PP15,358 P2
(45) Date of Patent: Nov. 23, 2004

(54) ***HEUCHERA* PLANT NAMED 'MIDNIGHT BURGUNDY'**

(50) Latin Name: *Heuchera×hybrida*
Varietal Denomination: Midnight Burgundy

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/775,948

(22) Filed: Feb. 10, 2004

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Heuchera* plant named 'Midnight Burgundy', characterized by its full, densely foliated and uniformly mounded plant habit; very dark purple-colored leaves, numerous showy white to light pink-colored flowers arranged on erect panicles; and excellent garden performance.

2 Drawing Sheets

Botanical classification/cultivar designation: *Heuchera× hybrida* cultivar Midnight Burgundy.

BACKGROUND OF THE INVENTION

The present invention relates to a new and distinct cultivar of *Heuchera* plant, botanically known as *Heuchera×hybrida* and hereinafter referred to by the name 'Midnight Burgundy'.

The new *Heuchera* is a product of a planned breeding program conducted by the Inventor in Scottdale, Pa. The objective of the breeding program is to create new *Heuchera* cultivars having good plant vigor, dense and uniform plant habit, and showy and attractive flower and leaf coloration.

The new *Heuchera* is a chemically-induced mutation of the *Heuchera×hybrida* cultivar Midnight Claret, not patented. The new *Heuchera* was discovered by the Inventor in a controlled environment in Scottdale, Pa. in August, 2001, from within a population of colchicine-treated plants of the cultivar Midnight Claret. The selection of this plant was based on its uniformity and vigor.

Asexual reproduction of the new *Heuchera* by cuttings in a controlled environment in Scottdale, Pa., since August, 2001, has shown that the unique features of this new *Heuchera* are stable and reproduced true to type in successive generations.

SUMMARY OF THE INVENTION

The cultivar Midnight Burgundy has not been observed under all possible environmental conditions. The phenotype may vary somewhat with variations in environment such as temperature and light intensity, without, however, any variance in genotype.

The following traits have been repeatedly observed and are determined to be the unique characteristics of 'Midnight Burgundy'. These characteristics in combination distinguish 'Midnight Burgundy' as a new and distinct cultivar of *Heuchera*:

1. Full, densely foliated and uniformly mounded plant habit.
2. Leaves very dark purple in color.

3. Numerous showy white to light pink-colored flowers arranged on erect panicles.
4. Excellent garden performance.

Plants of the new *Heuchera* can be compared to plants of the parent, the cultivar Midnight Claret. In side-by-side comparisons conducted by the Inventor in Scottdale, Pa., plants of the new *Heuchera* differed from plants of the cultivar Midnight Claret in the following characteristics:

1. Plants of the new *Heuchera* grew more uniformly and were move vigorous than plants of the cultivar Midnight Claret.
2. Flowers of plants of the new *Heuchera* had six petals, six sepals, six stamens and three pistils whereas flowers of plants of the cultivar Midnight Claret had five petals, five sepals, five stamens and two pistils.

Plants of the new *Heuchera* can be compared to plants of the cultivar Silver Light, disclosed in U.S. Plant patent application Ser. No. 10/324,932. In side-by-side comparisons conducted by the Inventor in Scottdale, Pa., plants of the new *Heuchera* differed from plants of the cultivar Silver Light in the following characteristics:

1. Plants of the new *Heuchera* and the cultivar Silver Light differed in leaf coloration.
2. Plants of the new *Heuchera* and the cultivar Silver Light differed in sepal and flower bud coloration.
3. Plants of the new *Heuchera* had thinner peduncles than plants of the cultivar Silver Light.
4. Flowers of plants of the new *Heuchera* had six petals, six sepals, six stamens and three pistils whereas flowers of plants of the cultivar Silver Light had five petals, five sepals, five stamens and two pistils.

Plants of the new *Heuchera* can also be compared to plants of the cultivar Jade Gloss, disclosed in U.S. Plant Pat. No. 13,137. In side-by-side comparisons conducted by the Inventor in Scottdale, Pa., plants of the new *Heuchera* differed from plants of the cultivar Jade Gloss in the following characteristics:

1. Plants of the new *Heuchera* and the cultivar Jade Gloss differed in leaf coloration.
2. Plants of the new *Heuchera* and the cultivar Jade Gloss differed in sepal coloration.
3. Plants of the new *Heuchera* had shorter peduncles than plants of the cultivar Jade Gloss.

4. Flowers of plants of the new *Heuchera* had six petals, six sepals, six stamens and three pistils whereas flowers of plants of the cultivar Jade Gloss had five petals, five sepals, five stamens and two pistils.

BRIEF DESCRIPTION OF THE PHOTOGRAPHS

The accompanying colored photographs illustrate the overall appearance of the new *Heuchera*, showing the colors as true as it is reasonably possible to obtain in colored reproductions of this type. Colors in the photographs may differ slightly from the color values cited in the detailed botanical description which accurately describe the colors of the new *Heuchera*.

The photograph on the first sheet comprises a side perspective view of a typical one-year old flowering plant of 'Midnight Burgundy'.

The photograph on the second sheet is a close-up view of a typical inflorescence of 'Midnight Burgundy'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following detailed botanical description describe plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: *Heuchera×hybrida* cultivar Midnight Burgundy.

Parentage: Chemically-induced mutation of the *Heuchera×hybrida* cultivar Midnight Claret, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright panicles with white to light pink-colored flowers. Vigorous growth habit.

*Plant size.*—Height, soil level to top of foliar plane: About 10 cm. Height, soil level to top of panicles: About 40 cm. Diameter or spread: About 20 cm.

*Foliage description.*—Arrangement: Basal rosette, simple. Length: About 6.5 cm. Width: About 6 cm. Shape: Rounded cordate; seven-lobed. Apex: Obtuse, lobed. Base: Auriculate. Margin: Crenate with fine ciliation. Texture, upper surface: Slightly rough; glabrous. Texture, lower surface: Slightly pubescent. Venation pattern: Palmate, reticulate. Color: Developing leaves, upper surface: 187B with interveinal blotches, 198D. Developing leaves, lower surface: 187B. Fully expanded leaves, upper surface: 187A underlain with 200A with interveinal blotches, 198D. Fully expanded leaves, lower surface: 187B. Venation, upper surface: Same as lamina. Venation, lower surface: 187A. Petiole: Length: About 8 cm. Diameter: About 2 mm. Texture, upper and lower surfaces: Pubescent. Color, upper and lower surfaces: 187A.

Flower description:

*Appearance/arrangement.*—Single campanulate flowers arranged on numerous erect panicles; about 80 to 120 flowers and flower buds per flowering stem. Flowers face outward to upright. Flowering continuous. Flowers persistent. Flowers not fragrant.

*Time of flowering.*—Plants flower June and July in Scottdale, Pa.

*Inflorescence longevity.*—Individual inflorescences last about one week on the plant.

*Inflorescence size.*—Length: About 40 cm. Diameter: About 7 cm.

*Flower size.*—Diameter: About 4.5 mm. Depth (height): About 7 mm.

*Flower buds.*—Height: About 3.5 mm. Diameter: About 2.5 mm. Shape: Globular. Color, at stage of showing color: 158A shaded with 57B.

*Sepals.*—Quantity/arrangement: Typically six sepals; radially symmetrical and fused at base. Calyx length: About 5 mm. Calyx diameter: About 4.5 mm. Shape: Elongate. Apex: Obtuse. Margin: Entire. Texture, upper and lower surfaces: Pubescent. Color, upper surface: Close to 155D shaded with 57B. Color, lower surface: Close to 155D heavily shaded with 57B.

*Petals.*—Quantity/arrangement: Typically six minute petals; radially symmetrical. Length: About 4 mm. Width: About 1.2 mm. Shape: Spatulate. Apex: Acute. Margin: Dentate. Texture, upper surface: Smooth. Texture, lower surface: Pubescent. Color, upper surface: Close to 155D. Color, lower surface: Close to 155D with glandular hairs, 57D.

*Flower bracts.*—Length: About 2.5 mm. Width: About 0.4 mm. Shape: Subulate. Apex: Acute. Margin: Entire with large spines. Texture, upper and lower surfaces: Pubescent. Color, upper and lower surfaces: 187B.

*Peduncle.*—Strength: Strong. Aspect: Upright. Length: About 25 cm. Diameter: About 2 mm. Texture: Smooth. Color: 187A.

*Pedicels.*—Strength: Strong. Aspect: About 60° from vertical. Length: About 3 mm. Diameter: About 0.2 mm. Texture: Pubescent. Color: 187B.

*Reproductive organs.*—Androecium: Stamen number: Typically six per flower. Anther shape: Oval. Anther length: About 0.4 mm. Anther color: 23A. Amount of pollen: None observed. Gynoecium: Pistil number: Typically three per flower. Pistil length: About 5.5 mm. Stigma shape: Round. Stigma color: 157C. Style length: About 3 mm. Style color: 157C. Ovary color: 157C.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Midnight Burgundy', as illustrated and described.

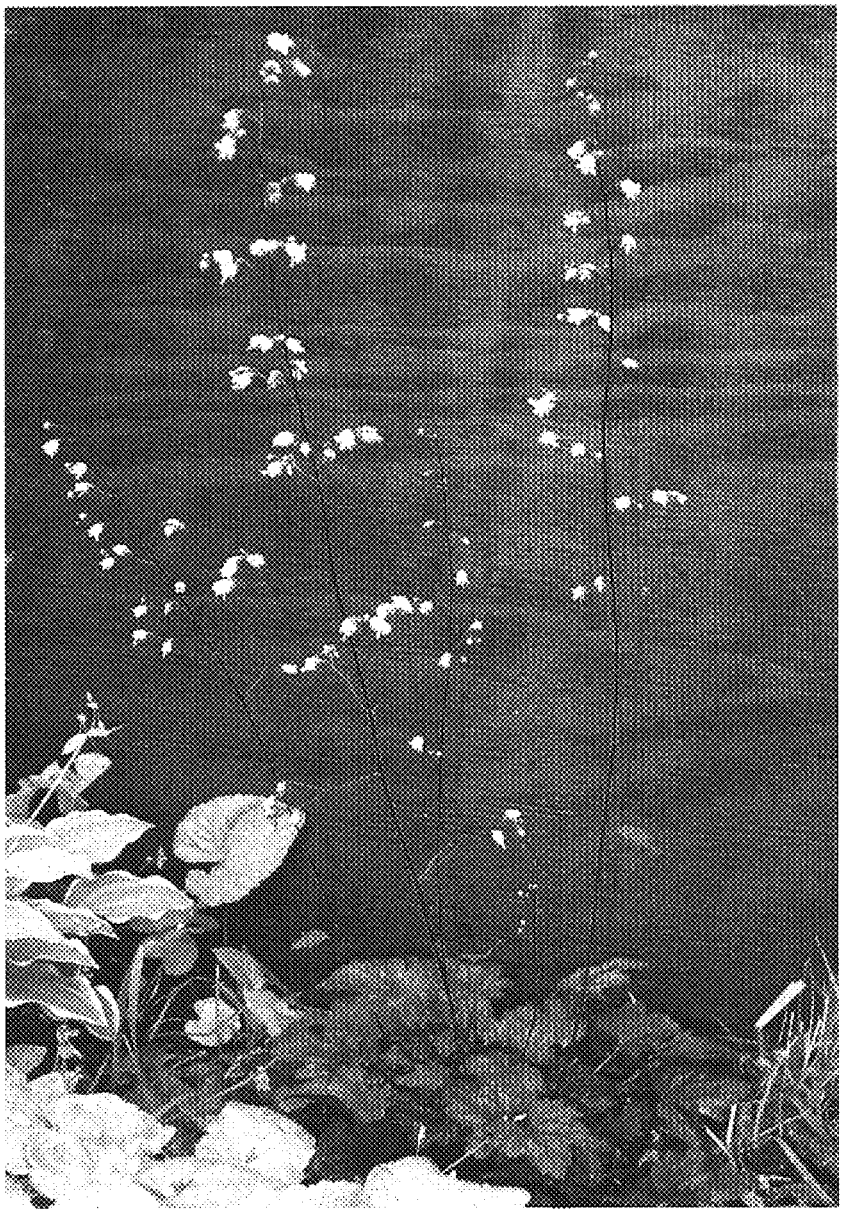

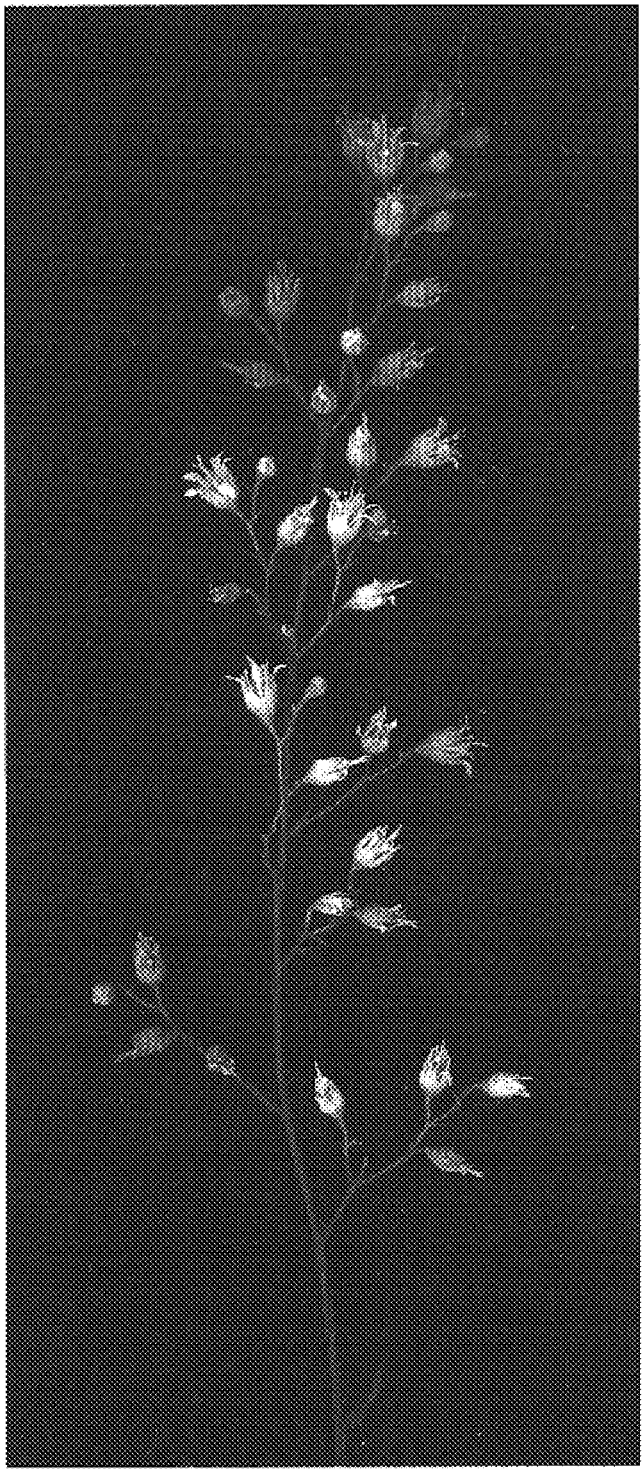

* * * * *